US00PP16690P2

(12) United States Plant Patent
Robb

(10) Patent No.: US PP16,690 P2
(45) Date of Patent: Jun. 20, 2006

(54) LAVENDER PLANT NAMED 'NINROS'

(50) Latin Name: *Lavandula stoechas*
Varietal Denomination: Ninros

(76) Inventor: John Robb, RMB 2117 Greta Road, Kulnurra NSW 2250 (AU)

( * ) Notice: Subject to any disclaimer, the term of this patent is extended or adjusted under 35 U.S.C. 154(b) by 47 days.

(21) Appl. No.: 11/113,370

(22) Filed: Apr. 23, 2005

(51) Int. Cl.
*A01H 5/00* (2006.01)

(52) U.S. Cl. ..... Plt./226
(58) Field of Classification Search ..... Plt./226
See application file for complete search history.

(56) References Cited

U.S. PATENT DOCUMENTS

PP12,599 P2 * 4/2002 Cherry ..... Plt./226
PP14,205 P2 * 10/2003 Cherry ..... Plt./226

* cited by examiner

*Primary Examiner*—Kent Bell
*Assistant Examiner*—W. C. Haas
(74) *Attorney, Agent, or Firm*—C. A. Whealy

(57) ABSTRACT

A new and distinct cultivar of Lavender plant named 'Ninros', characterized by its compact, upright, somewhat outwardly spreading and mounded plant habit; freely branching habit, dense and bushy plant form; early flowering habit; and red purple-colored flowers with pale pink-colored terminal flower bracts.

1 Drawing Sheet

Botanical designation: *Lavandula stoechas.*
Cultivar denomination: 'Ninros'.

CROSS-REFERENCE TO RELATED APPLICATIONS

The present application is co-pending with the following related applications: U.S. Plant patent application Ser. No. 11/113,387, Lavender Plant Named 'Ninlip'; U.S. Plant patent application Ser. No. 11/113,389, Lavender Plant Named 'Ninpur'; U.S. Plant patent application Ser. No. 11/113,392, Lavender Plant Named 'Ninwhi'.

BACKGROUND OF THE INVENTION

The present Invention relates to a new and distinct cultivar of Lavender plant, botanically known as *Lavandula stoechas,* and hereinafter referred to by the name 'Ninros'.

The new Lavender is a product of a planned breeding program conducted by the Inventor in Kulnura, New South Wales, Australia. The objective of the breeding program was to create new very compact, mounded and freely branching Lavender cultivars with attractive flowers and good garden performance.

The new Lavender originated from an open-pollination in 1999 of a proprietary selection of *Lavandula stoechas* identified as code number 99-54, not patented, as the female, or seed, parent with an unknown selection of *Lavandula stoechas,* as the male, or pollen, parent. The new Lavender was discovered and selected by the Inventor as a single flowering plant within the progeny of the stated open-pollination grown in a controlled environment in Kulnura, New South Wales, Australia in September, 2000.

Asexual reproduction of the new cultivar by terminal cuttings at Kulnura, New South Wales, Australia, since 2000, has shown that the unique features of this new Lavender are stable and reproduced true to type in successive generations.

SUMMARY OF THE INVENTION

Plants of the cultivar 'Ninros' have not been observed under all possible environmental conditions. The phenotype may vary somewhat with variations in environment such as temperature and light intensity without, however, any variance in genotype.

The following traits have been repeatedly observed and are determined to be the unique characteristics of 'Ninros'. These characteristics in combination distinguish 'Ninros' as a new and distinct cultivar:

1. Compact, upright, somewhat outwardly spreading and mounded plant habit.
2. Freely branching habit, dense and bushy plant form.
3. Early flowering habit.
4. Red purple-colored flowers with pale pink-colored terminal flower bracts.

Plants of the new Lavender differ from plants of the female parent selection in the following characteristics:

1. Plants of the new Lavender are more uniform in plant habit than plants of the female parent selection.
2. Plants of the new Lavender and the female parent selection differ in flower coloration.
3. Plants of the new Lavender and the female parent selection differ in flower bract coloration.

Plants of the new Lavender differ primarily from plants of the cultivars 'Ninlip', disclosed in U.S. Plant patent application Ser. No. 11/113,387; 'Ninpur', disclosed in U.S. Plant patent application Ser. No. 11/113,389; and 'Ninwhi', disclosed in U.S. Plant patent application Ser. No. 11/113,392, in flower and terminal flower bract coloration.

Plants of the new Lavender can be compared to plants of the Lavender cultivar Kew Red, not patented. In side-by-side comparisons conducted in Kulnura, New South Wales, Australia, plants of the new Lavender differed from plants of the cultivar Kew Red primarily in flower and terminal bract coloration, inflorescence size, terminal flower bract size and peduncle length.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new Lavender.

The photograph at the top of the sheet comprises a side perspective view of a typical flowering plant of 'Ninros' grown in a container.

The photograph at the bottom of the sheet comprises a close-up view of a typical inflorescence of 'Ninros'.

DETAILED BOTANICAL DESCRIPTION

In the following description, color references are made to The Royal Horticultural Society Colour Chart, 1999 Edition, except where general terms of ordinary dictionary significance are used. Plants used for the aforementioned photographs and following description were grown under conditions which closely approximate commercial production conditions during the winter and spring in a polycarbonate-covered greenhouse in Melbourne, New South Wales, Australia for about six months in one-gallon containers. Plants were pinched twice. During the production of the plants, day temperatures ranged from 18° C. to 30° C., night temperatures ranged from 8° C. to 18° C. and light levels ranged from 5,000 to 9,000 foot-candles.

Botanical classification: *Lavandula stoechas* cultivar 'Ninros'.

Parentage:

*Female, or seed, parent.*—Proprietary selection of *Lavandula stoechas* identified as code number 99-54, not patented.

*Male, or pollen, parent.*—Unknown selection of *Lavandula stoechas,* not patented.

Propagation:

*Type cutting.*—Terminal vegetative cuttings.

*Time to initiate roots, summer.*—About one week at 25° C.

*Time to initiate roots, winter.*—About two weeks at 20° C.

*Time to produce a rooted young plant, summer.*—About six weeks at 25° C.

*Time to produce a rooted young plant, winter.*—About seven weeks at 20° C.

*Root description.*—Fine, fibrous.

*Rooting habit.*—Freely branching.

Plant description:

*Form.*—Perennial plant; compact, upright, somewhat outwardly spreading and mounded plant form. Freely branching habit with lateral branches potentially at every node; dense and bushy plant habit. Flowers in verticillasters on crowded spikes with showy terminal flower bracts.

*Plant height.*—About 40 cm.

*Plant width.*—About 40 cm.

*Lateral branch description.*—Length: About 15 cm to 20 cm. Diameter: About 5 mm. Internode length: About 1 cm to 2 cm. Strength: Strong. Aspect: Mostly upright to somewhat outwardly. Texture, immature: Pubescent. Texture, mature: Woody. Color, immature: 144C. Color, mature: 141C.

*Foliage description.*—Arrangement: Opposite, simple; sessile. Length: About 2 cm. Width: About 3 mm. Shape: Linear. Apex: Rounded. Base: Attenuate, clasping. Margin: Entire. Texture, upper and lower surfaces: Pubescent. Fragrance: Very aromatic, pungent. Venation pattern: Pinnate; reticulate. Color: Developing foliage, upper and lower surfaces: 137B. Fully expanded foliage, upper and lower surfaces: 137B. Venation, upper and lower surfaces: 137B.

Flower description:

*Flower arrangement and shape.*—Small single flowers in compact verticillasters on crowded spikes. Freely flowering, about eight whorls each with about ten open flowers and flower buds per spike; flowers tubular with five lobes; inflorescences with showy terminal bracts.

*Natural flowering season.*—Continuous throughout the Spring. Time to flowering: Early flowering, plants begin to flower about three months after planting.

*Flower longevity on the plant.*—Individual inflorescences last about two weeks on the plant and individual flowers last about three days on the plant. Flowers, not persistent; terminal flower bracts, persistent.

*Flower buds.*—Length: About 4 mm. Diameter: About 2 mm. Shape: Oblong. Color: 74B.

*Inflorescence size.*—Height: About 1.5 cm. Diameter: About 1 cm.

*Flowers.*—Diameter: About 1 mm to 2 mm. Depth (height): About 4 mm to 5 mm.

*Petals.*—Arrangement: Five, fused into a tube. Length, lobes: About 1 mm. Width, lobes: About 1.5 mm. Tube length: About 1 mm. Shape: Roughly spatulate. Apex: Rounded. Margin: Entire. Texture, upper and lower surfaces: Smooth, glabrous; velvety. Color: When opening, upper and lower surfaces: 74B. Fully opened, upper and lower surfaces: 74B.

*Terminal flower bracts.*—Arrangement: About four in a single whorl at inflorescence apex. Length: About 1.7 cm. Width: About 8 mm. Shape: Oblong. Apex: Rounded to slightly acute. Base: Obtuse. Margin: Entire. Texture, upper and lower surfaces: Smooth, glabrous; velvety. Color, immature, upper and lower surfaces: Close to 73D. Color, mature, upper and lower surfaces: Close to 73D; venation, close to 144A overlain with 81B.

*Flower bracts.*—Arrangement: Each whorl of flowers subtended by a flower bract. Length: About 7 mm. Width: About 8 mm. Shape: Broadly ovate. Apex: Acute. Base: Truncate. Margin: Entire. Texture, upper and lower surfaces: Smooth. Color, upper and lower surfaces: 147C; venation, 147C.

*Calyx.*—Arrangement: Five sepals fused into a tube. Length: About 3 mm. Width: About 1.5 mm. Sepal apex: Acute. Color, immature and mature, upper and lower surfaces: 138B.

*Peduncle.*—Strength: Strong. Length: About 3 cm to 5 cm. Diameter: About 1 mm. Aspect: Mostly upright. Color: 144D.

*Reproductive organs.*—Stamens: Quantity per flower: Four. Anther shape: Oval. Anther length: Less than 1 mm. Anther color: Yellow. Pollen amount: Scarce. Pollen color: Yellow. Pistils: Quantity per flower: One. Pistil length: About 5 mm. Stigma shape: Rounded. Stigma color: White. Style length: About 3 mm to 4 mm. Style color: White. Ovary color: Close to 144B.

*Seed/fruit.*—Seed and fruit production has not been observed.

Disease/pest resistance: Plants of the new Lavender have not been noted to be resistant to pathogens and pests common to Lavender.

Weather tolerance: Plants of the new Lavender have exhibited good tolerance to rain and wind and have been observed to tolerate temperatures from −2° C. to 40° C.

It is claimed:

1. A new and distinct cultivar of Lavender plant named 'Ninros', as illustrated and described.

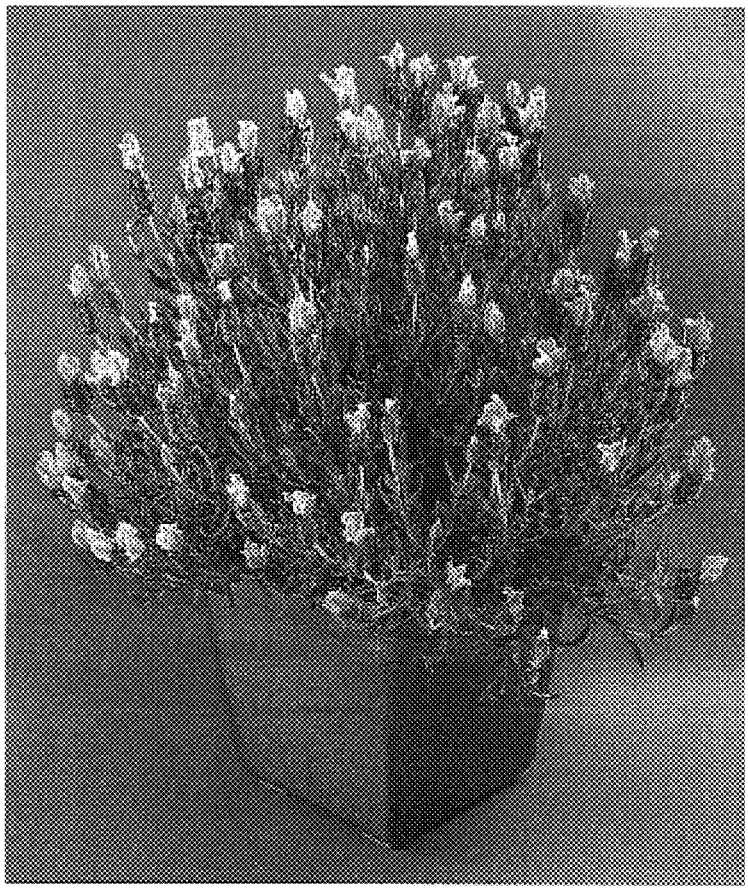
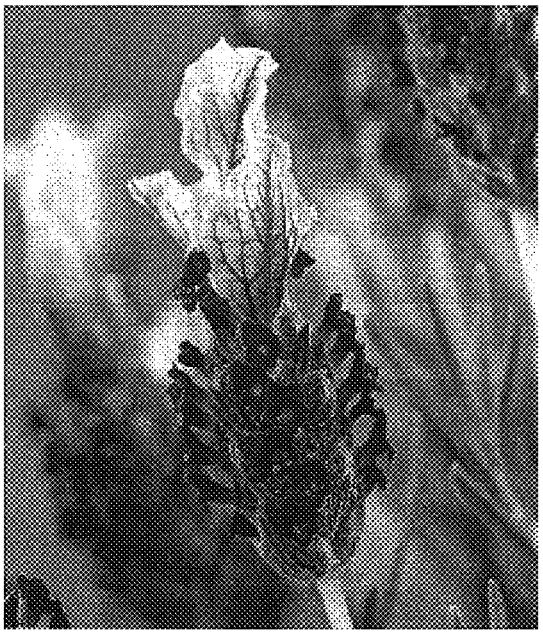

* * * * *